United States Patent
McLean et al.

(10) Patent No.: US 7,997,729 B2
(45) Date of Patent: Aug. 16, 2011

(54) METHOD FOR CORRECTING PATIENT MOTION WHEN OBTAINING RETINA VOLUME USING OPTICAL COHERENCE TOMOGRAPHY

(75) Inventors: Duncan McLean, Kingston (CA); Justin Pedro, Waterloo (CA); Clive Hayward, Kingston (CA)

(73) Assignee: OTI Ophthalmic Technologies Inc. (CA)

( * ) Notice: Subject to any disclaimer, the term of this patent is extended or adjusted under 35 U.S.C. 154(b) by 265 days.

(21) Appl. No.: 12/247,858

(22) Filed: Oct. 8, 2008

(65) Prior Publication Data

US 2009/0103049 A1 Apr. 23, 2009

Related U.S. Application Data

(60) Provisional application No. 60/981,216, filed on Oct. 19, 2007.

(51) Int. Cl.
*A61B 3/14* (2006.01)
*A61B 3/10* (2006.01)
*A61B 3/00* (2006.01)

(52) U.S. Cl. .......... 351/206; 351/221; 351/246
(58) Field of Classification Search .......... 351/200–246
See application file for complete search history.

(56) References Cited

U.S. PATENT DOCUMENTS

| | | | | |
|---|---|---|---|---|
| 5,493,109 | A * | 2/1996 | Wei et al. | 250/201.3 |
| 7,480,058 | B2 * | 1/2009 | Zhao et al. | 356/497 |
| 7,593,559 | B2 * | 9/2009 | Toth et al. | 382/128 |
| 7,712,898 | B2 * | 5/2010 | Abramoff et al. | 351/206 |

* cited by examiner

*Primary Examiner* — Mohammed Hasan
(74) *Attorney, Agent, or Firm* — Richard J. Mitchell; Marks & Clerk

(57) ABSTRACT

A computer-implemented method of correcting for motion of a sample during OCT imaging obtains a series of cross-sectional volume scans through the sample at different positions on a first coordinate axis, obtains at least two cross-sectional alignment scans in planes intersecting said volume scans at an angle, and stores the alignment scans and the volume scans in memory. The alignment scans are matched to the volume scans at lines of intersection thereof to determine the relative displacement of the volume scans to the sample due to sample motion. The relative displacement is used to correct for motion of the sample between successive volume scans.

5 Claims, 2 Drawing Sheets

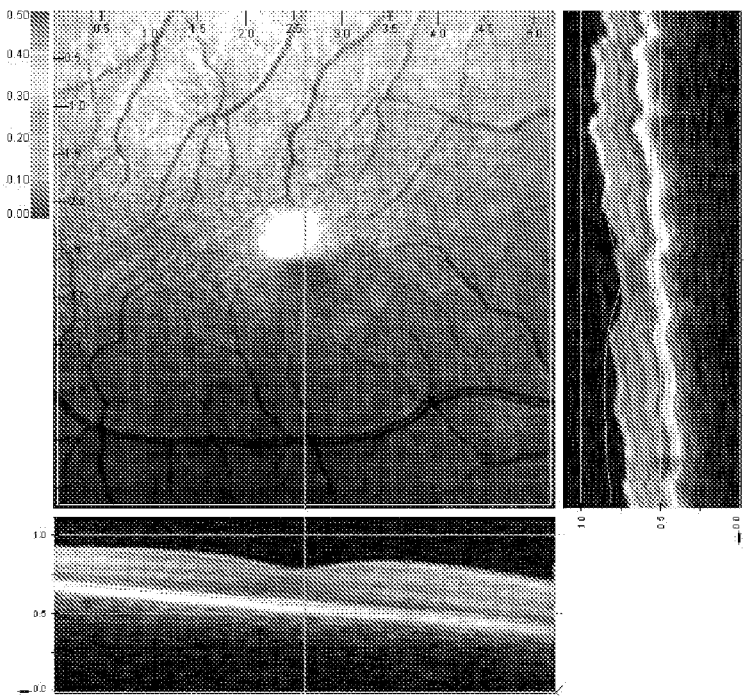
Fig. 3A
Fig. 3B
Fig. 3C
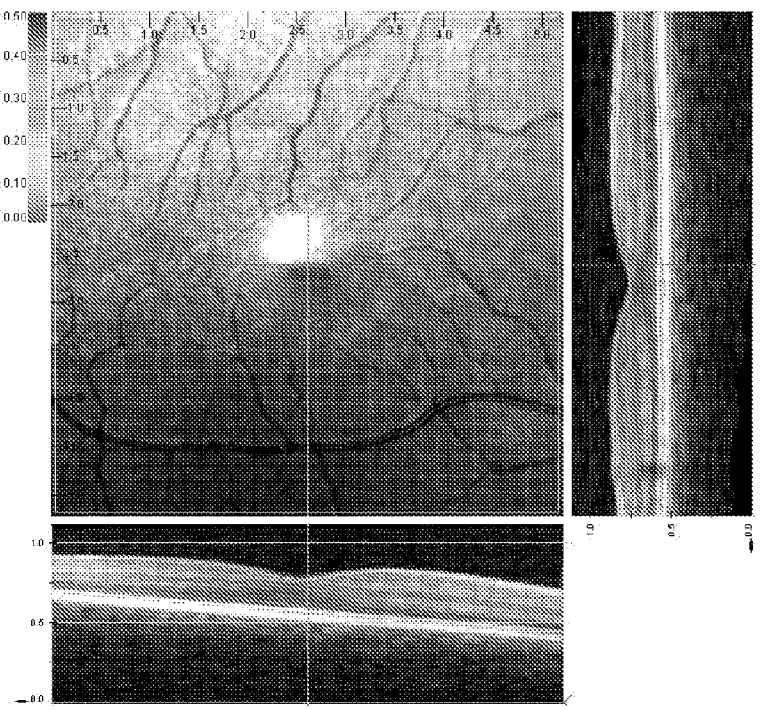
Fig. 4A
Fig. 4B
Fig. 4C

US 7,997,729 B2

METHOD FOR CORRECTING PATIENT MOTION WHEN OBTAINING RETINA VOLUME USING OPTICAL COHERENCE TOMOGRAPHY

CROSS REFERENCE TO RELATED APPLICATION

This application claims the benefit under 35 USC 119(e) of prior U.S. provisional application No. 60/981,216, the contents of which are herein incorporated by reference.

FIELD OF THE INVENTION

This invention relates to the field of optical coherence tomography imaging, and in particular to a method of correcting patient motion while taking scans of the eye.

BACKGROUND OF THE INVENTION

Optical coherence tomography (OCT) is an imaging technique that makes possible the three dimensional imaging of transparent or semi-transparent objects, such body tissues, specifically eye. OCT is described in detail in U.S. Pat. No. 6,769,769, the contents of which are herein incorporated by reference.

Using Optical Coherence Tomography (OCT) it is possible to rapidly obtain a line of image information extending in the z direction, where the z axis extends in the depth direction. Such a scan is known as an A-scan. In time domain OCT, this can be done by changing the optical path difference between the reference beam and object beam in the interferometer to cause the "coherence gate," or region where the optical path difference is less than the coherence length, to move back and forth in the depth direction. Image information is obtained from the position of the coherence gate. In spectral OCT, by analyzing the spectrum of the returned signal, a complete line of information in the z direction can be obtained from a signal measurement.

By moving the interferometer beam along the x or y axes (or any other plane orthogonal to the x-y plane), it is possible to obtain a B-scan. This is a sectional scan through the sample in the depth direction.

These depth images, or B Scans, can in turn be collected in a raster pattern to obtain a volume image of the tissue. However, in the case of imaging the eye, which is an important application of OCT, patient movement due to breathing, heartbeat, inability to fixate, or any other reason causes the captured B Scans to be mis-aligned.

SUMMARY OF THE INVENTION

In accordance with embodiments of the invention, the multiple B-scan images are aligned so that the volume in three dimensions can be reconstructed to look as much like the tissue as possible. The method eliminates motion artifacts caused by patient movement during the capture of OCT volumes. The method will only correct for vertical motion on a B Scan, i.e. the patient moving towards and away from the lens barrel of the OCT scanner.

Thus, according to the present invention there is provided a computer-implemented method of correcting for motion of a sample during OCT imaging, comprising obtaining a series of cross-sectional volume scans through the sample at different positions on a first coordinate axis; obtaining at least two cross-sectional alignment scans in planes intersecting said volume scans at an angle; storing said alignment scans and said volume scans in memory; matching said alignment scans and said volume scans at lines of intersection thereof to determine the relative displacement of said volume scans to the sample due to sample motion; and using said relative displacement to correct for motion of the sample between successive volume scans.

According to a second aspect of the invention there is provided an apparatus for correcting for sample movement during OCT imaging, comprising a memory; a data structure in said memory comprising a series of cross-sectional volume scans at known positions in the sample and cross-sectional alignment scans in planes intersecting said volume scans at an angle; and a computer for processing said series of cross-sectional volume scans to obtain a volume scan of the sample, and wherein said alignment scans and said volume scans are matched at lines of intersection thereof to determine the relative displacement of said volume scans to the sample due to sample motion and said relative displacement is used to correct for motion of the sample between successive volume scans.

The sample is typically the eye, but the invention is equally applicable to other transparent or semi-transparent samples subject to movement between scans.

BRIEF DESCRIPTION OF THE DRAWINGS

The invention will now be described in more detail, by way of example only, with reference to the accompanying drawings, in which:—

FIGS. 3A to 3C show an en-face image, a horizontal section and vertical section respectively of a non motion-corrected volume; and FIGS. 4A to 4C are similar images to FIGS. 2A to 2C of a motion corrected volume.

DESCRIPTION OF THE PREFERRED EMBODIMENTS

Figure 1:
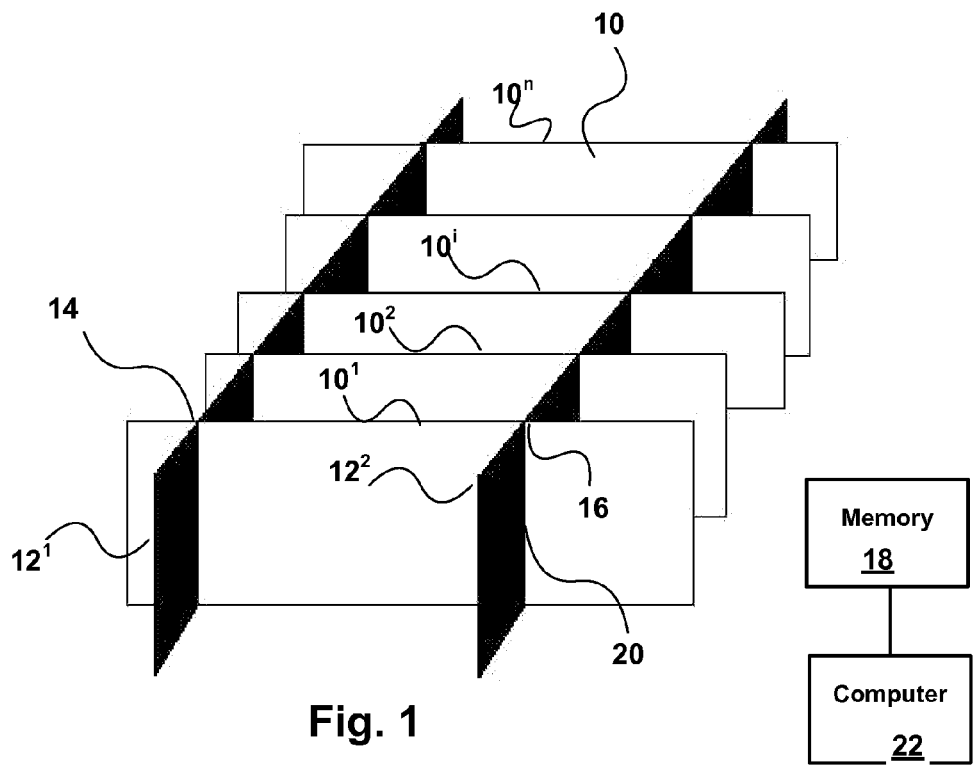
FIG. 1 shows a possible scanning pattern in accordance with an embodiment of the invention.

In accordance with an embodiment of the invention, the sample to be scanned is scanned in the pattern shown in FIG. 1. Here, the frames 10 are successive B volume scans that are used to construct a three dimensional volume image of the sample. By taking a series of B scans in the y-z plane, at different positions along the x coordinate, it is possible to obtain complete three dimensional image information of the sample.

Figure 2:
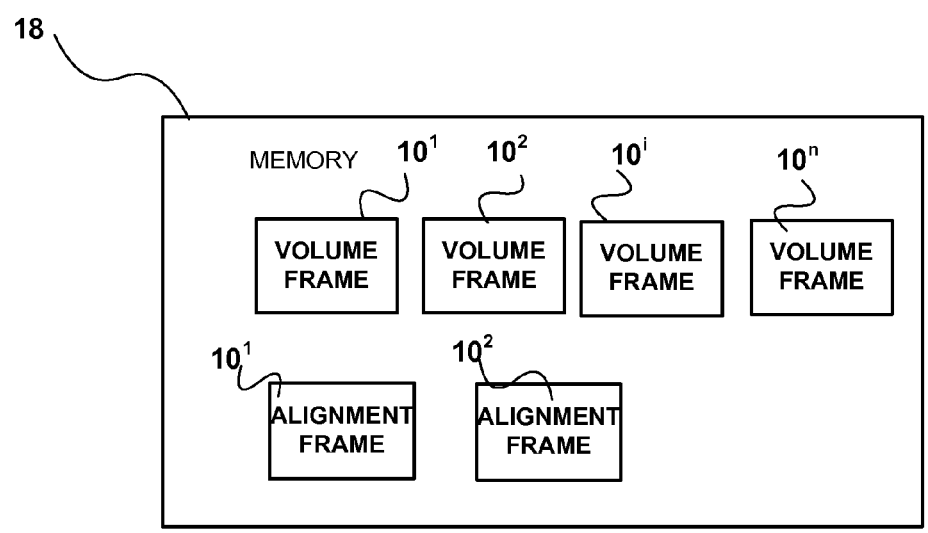
FIG. 2 shows a data structure in memory 18 containing the volume scans and alignment scans.

The frames $12^1$, $12^2$ are alignment or reference frames taken at 90 degrees to the volume frames 10 and at positions 14, 16, ⅓ and ⅔ of the way across the volume frames 10. The scanned frames are stored in a memory 18 associated with computer 22. The memory includes a data structure comprising the image information for each of the B-scan volume frames 10 and the reference frames 12 as showing FIG. 2.

If the patient moves, as is likely, during the taking of the series of B-scans 10, the B-scans will be shifted laterally relative to each other with reference to the eye. For example, if the B-scans are separated by a distance d in the x direction, and between the taking of two adjacent scans, the patient's eye moves by a distance δd, the actual position of the second scan relative to the eye will be d±δd depending on the direction of movement. By matching the alignment frames to the B-scan frames along their intersection lines, this lateral motion can be compensated and patient motion corrected. For example, assume between scans that the second frame $10^2$ shifted away from the first frame $10^1$ by an amount δd relative to the eye. δd is not known. However, the intersection line 20 of frames 10 and 12 is common to both frames, so by matching image line on frame $10^2$ with a series of parallel image lines on the intersecting frames $12^1$, $12^2$, it is possible to find the actual position relative to the eye of the frame $10^2$.

The B scans 10 are gathered in a raster pattern or some other equivalent manner such that all frames are parallel and obtained from known locations relative to an external reference. The order in which the B Scans 10 are collected is irrelevant so long their relative positions are known.

The extra alignment B Scan frames $12^1$, $12^2$ are collected immediately before or after the B Scans that make up the volume are collected. The extra frames are taken at some known angle, 90 degrees in this example, to the B Scans that make up the volume and they are taken at known positions with respect to the B Scans that make up the volume (ex. ⅓ and ⅔ of the B Scan width).

The extra frames $12^1$, $12^2$ are then used as benchmarks to align volume frames 10 on along the intersection lines 20 in the manner described. Statistical methods can be used to find the best fit for the volume B Scan frames on the alignment B Scan frames. Alternatively, boundary detection can be used to find different tissue layers on the alignment and volume B Scans which can then be used to align the two frames.

The alignment scans $12^1$, $12^2$, and volume scans $10^1$, $10^2$, $10^i$, $10^n$ are then form a data structure in memory 18. These scans are subsequently processed by computer 22 to create the motion corrected image.

Once the proper alignment positions of each B scan volume frame have been determined, the in-memory representation of the volume can be shifted into the appropriate position. This corrected volume can either be saved to external media (ex hard drive), or kept as a pure in-memory representation.

FIGS. 2A-2C shows an example of an OCT volume that has not been motion corrected. It will be observed that the horizontal image (FIG. 2B) is sharp. That is because it is a true B Scan, that is, it corresponds to the frames 10 from FIG. 1. The vertical frame, however, is a reconstructed B scan; all of the horizontal B scans are used to interpolate the vertical frame. The vertical frame should look very similar to the horizontal frame, but instead it looks fuzzy because the patient moved during the scans.

FIGS. 3A to 3C shows the exact same OCT volume after it has been motion corrected using the alignment frames as described above. It will be seen that in this figure the vertical frame is now much smoother.

Example

The following is an algorithm for motion correcting frames assuming that the alignment frames are from ⅓ and ⅔ or the way across each volume frame. The algorithm can be implemented in computer 22.

The use of 10 column wide sections of image is arbitrary here; any value from 1 to half of the image width could be used:

```
For each volume frame
{
   extract 10 columns from the volume frame at ⅓ of it's width
   smooth the 10 column wide image
   collapse the 10 column wide image into 1 column
   extract 10 columns from the ⅓ alignment frame at the relative
 position the above frame is from
   smooth the 10 column wide image
   collapse the 10 column wide image into 1 column
   use statistical methods to determine the best fit for the two images.
   extract 10 columns from the volume frame at ⅔ of its width
   smooth the 10 column wide image
   collapse the 10 column wide image into 1 column
   extract 10 columns from the ⅔ alignment frame at the relative
 position the above frame is from
   smooth the 10 column wide image
   collapse the 10 column wide image into 1 column
   use statistical methods to determine the best fit for the two images.
   Use the two alignment values to determine an absolute shift up
 or down for the whole image.
   Use the two alignment values to determine a relative slope
   the image should be on
   Use the absolute shift and the slope to shift each column of
 the image into its proper location
}
```

The invention claimed is:

1. A computer-implemented method of correcting for motion of a sample during OCT imaging, comprising:
   obtaining a series of OCT cross-sectional volume scans in parallel planes through the sample at different positions on a first coordinate axis;
   obtaining at least two OCT cross-sectional alignment scans in planes intersecting said parallel planes containing said volume scans at an angle;
   storing said alignment scans and said volume scans in memory; and
   matching said alignment scans and said volume scans at lines of intersection thereof to determine the relative displacement of said volume scans to the sample due to sample motion; and
   using said relative displacement to correct for motion of the sample between successive volume scans.

2. A method as claimed in claim 1, wherein said angle is ninety degrees.

3. A method as claimed in claim 1, wherein the sample is the retina of an eye.

4. Apparatus for correcting for sample movement during OCT imaging, comprising:
   a memory;
   a data structure in said memory comprising a series of OCT cross-sectional volume scans in known parallel planes in the sample and OCT cross-sectional alignment scans in planes intersecting said known parallel planes containing said cross-sectional volume scans at an angle; and
   a computer for processing said series of cross-sectional volume scans to obtain a volume scan of the sample, and wherein said alignment scans and said volume scans are matched at lines of intersection thereof to determine the relative displacement of said volume scans to the sample due to sample motion and said relative displacement is used to correct for motion of the sample between successive volume scans.

5. An apparatus as claimed in claim 4, wherein said angle is ninety degrees.

* * * * *